(12) United States Patent
Pulugurtha

(10) Patent No.: US 10,821,011 B2
(45) Date of Patent: Nov. 3, 2020

(54) MEDICAL DEVICE AND METHOD OF MANUFACTURING USING MICRO-CLADDING TO FORM FUNCTIONALLY GRADED MATERIALS

(71) Applicant: Medtronic Vascular, Inc., Santa Rosa, CA (US)

(72) Inventor: Syamala Pulugurtha, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 43 days.

(21) Appl. No.: 15/917,816

(22) Filed: Mar. 11, 2018

(65) Prior Publication Data

US 2019/0274854 A1     Sep. 12, 2019

(51) Int. Cl.
| | |
|---|---|
| *A61F 2/82* | (2013.01) |
| *A61F 2/915* | (2013.01) |
| *A61L 31/18* | (2006.01) |
| *A61L 31/02* | (2006.01) |
| *B23K 26/342* | (2014.01) |
| *B22F 3/105* | (2006.01) |
| *B22F 7/06* | (2006.01) |
| *B33Y 10/00* | (2015.01) |

(Continued)

(52) U.S. Cl.
CPC ............ *A61F 2/915* (2013.01); *A61L 31/022* (2013.01); *A61L 31/18* (2013.01); *B22F 3/1055* (2013.01); *B22F 7/06* (2013.01); *B23K 26/342* (2015.10); *B33Y 10/00* (2014.12); *B33Y 80/00* (2014.12); *A61F 2002/91575* (2013.01); *A61F 2240/001* (2013.01); *A61F 2250/0018* (2013.01); *A61F 2250/0032* (2013.01); *A61F 2250/0098* (2013.01); *B22F 2003/1058* (2013.01); *B23K 2101/04* (2018.08)

(58) Field of Classification Search
CPC ........................................................ A61F 2/82
See application file for complete search history.

(56) References Cited

U.S. PATENT DOCUMENTS

| | | |
|---|---|---|
| 6,676,892 B2 | 1/2004 | Das et al. |
| 8,052,743 B2 | 11/2011 | Weber et al. |

(Continued)

OTHER PUBLICATIONS

International Search Report and Written Opinion, issued in International Application No. PCT/US2019/021608, dated Jun. 17, 2019.

(Continued)

*Primary Examiner* — Matthew W Schall

(57) ABSTRACT

A method of making a method of making a stent includes forming a precursor stent using micro-cladding. The precursor stent includes a plurality of bands made of a first material disposed adjacent to each other and a plurality of connectors connecting each band to an adjacent band. The precursor stent includes a plurality of first connectors configured to remain and a plurality of second connectors made by functionally grading the first material with a second material to create embrittlement. The plurality of second connectors are configured to be removed. The precursor stent is processed to remove the plurality of second connectors without adversely affecting the bands and the plurality of first connectors. The second material may be a radiopaque material.

27 Claims, 11 Drawing Sheets

(51) Int. Cl.
*B33Y 80/00* (2015.01)
*B23K 101/04* (2006.01)

(56) References Cited

U.S. PATENT DOCUMENTS

| | | | |
|---|---|---|---|
| 8,089,029 B2 | 1/2012 | Flanagan | |
| 8,353,952 B2 | 1/2013 | Thompson et al. | |
| 8,903,533 B2 | 12/2014 | Eggers et al. | |
| 9,114,032 B1 | 8/2015 | Pulugurtha | |
| 9,643,281 B1 | 5/2017 | Memmen et al. | |
| 2005/0182479 A1 | 8/2005 | Bonsignore et al. | |
| 2006/0079953 A1 | 4/2006 | Gregorich et al. | |
| 2006/0122694 A1 | 6/2006 | Stinson et al. | |
| 2007/0061007 A1 | 3/2007 | Nolting | |
| 2007/0213810 A1* | 9/2007 | Newhauser | A61F 2/91 623/1.16 |
| 2007/0219626 A1 | 9/2007 | Rolando et al. | |
| 2008/0131479 A1 | 6/2008 | Weber et al. | |
| 2010/0087910 A1 | 4/2010 | Weber | |
| 2010/0228369 A1 | 9/2010 | Eggers et al. | |
| 2010/0291401 A1 | 11/2010 | Medina et al. | |
| 2011/0067778 A1 | 3/2011 | Mitchell et al. | |
| 2011/0070357 A1 | 3/2011 | Mitchell et al. | |
| 2011/0070358 A1 | 3/2011 | Mauch et al. | |
| 2012/0067454 A1 | 3/2012 | Melder | |
| 2012/0067455 A1 | 3/2012 | Mitchell et al. | |
| 2012/0070562 A1 | 3/2012 | Avelar et al. | |
| 2012/0070563 A1 | 3/2012 | Mitchell et al. | |
| 2013/0331927 A1 | 12/2013 | Zheng et al. | |
| 2014/0277375 A1 | 9/2014 | Weier et al. | |
| 2015/0010422 A1 | 1/2015 | Nash | |
| 2016/0229127 A1 | 8/2016 | Halliday et al. | |
| 2016/0368054 A1 | 12/2016 | Ng et al. | |
| 2016/0375490 A1 | 12/2016 | Marchione | |
| 2017/0072636 A1 | 3/2017 | Ng et al. | |
| 2017/0189965 A1 | 7/2017 | Vaidya et al. | |
| 2019/0039137 A1 | 2/2019 | Hildreth et al. | |

OTHER PUBLICATIONS

Barnett, "Weak support material techniques for alternative additive manufacturing materials," 2015, Additive Manufacturing 8 (2015) 95-104 (Year: 2015).

Denny, et al., "Triple Hopper Powder Feeder System for Variable Composition Laser Cladding", Laser Materials Processing, vol. 77, Oct. 24-28, 1993.

Jhabvala, "An innovative method to build support structures with a pulsed laser in the selective laser melting process," 2012, Int J Adv ManufTechnol (2012) 59:137-142 (Year: 2012).

Jhabvala "On the effect of scanning strategies in the selective laser melting process," Virtual and Physical Prototyping • Jun. 2010 ( Year: 2010).

\* cited by examiner

MEDICAL DEVICE AND METHOD OF MANUFACTURING USING MICRO-CLADDING TO FORM FUNCTIONALLY GRADED MATERIALS

FIELD OF THE INVENTION

The invention relates generally to methods of making a medical device, and more particularly to a method of making a stent using a micro-cladding manufacturing process to form functionally graded materials.

BACKGROUND OF THE INVENTION

A wide range of medical treatments exist that utilize medical devices including stents or endoluminal prostheses. As used herein, the term "stent" is intended to cover medical devices that are adapted for temporary or permanent implantation within a body lumen, including both naturally occurring and artificially made lumens, such as, but not limited to: arteries, whether located within the coronary, mesentery, peripheral, or cerebral vasculature; veins; gastrointestinal tract; biliary tract; urethra; trachea; hepatic shunts; and fallopian tubes.

Accordingly, different stents have been developed, each providing a uniquely beneficial structure to modify the mechanics of the targeted lumen wall. For example, stent prostheses are known for implantation within body lumens to provide artificial radial support to the wall tissue, which forms the various lumens within the body.

Stents have been made by a variety of methods, including forming a wire into a waveform and helically wrapping the waveform around a mandrel, removing material from a tubular cylinder such as by a laser to leave a stent (sometimes referred to as a tubular slotted stent or laser cut stent), and forming individual cylindrical components and attaching adjacent cylindrical components to each other to form a tube. Such methods can be laborious, expensive, and time-consuming. It would be desirable to use additive manufacturing techniques to make stents and other medical devices. However, additive manufacturing techniques may be limited in making certain shapes for medical devices, and particularly for certain shapes of stents. For example, and not by way of limitation, certain medical devices that are generally tubular, such as stents, may be formed by additive manufacturing by building the medical device vertically. In other words, the longitudinal axis of the medical device is perpendicular to the surface or substrate upon which the medical device is built. In additive manufacturing, layers, also referred to as clads of material for the medical device, are built upon previous layers of the material. In certain medical devices, such as certain stents, it is desirable for a significant portion of a perimeter of a first portion of the device to not be connected to a second portion of the device. For example, and not by way of limitation, in a stent with a plurality of bands formed from struts and crowns, it is often desirable for only some of the crowns of a band to be connected to crowns of an adjacent band. However, when building such a stent vertically by additive manufacturing as described above, it is desirable for connectors to be built between most or all of the crowns of adjacent bands in order to provide a support for the following layer of material.

In a solution described in U.S. Pat. No. 9,114,032 assigned to Medtronic Vascular, Inc. and incorporated by reference herein in its entirety, connectors are formed between crowns of a stent by additive manufacturing. However, some of the connectors are then removed by laser removal, chemical etching, or other methods. Removal of connectors after being formed requires additional steps and care must be taken to avoid adversely affecting the remaining stent components during removal of the unwanted connectors.

Further, medical devices such as stents are made from a variety of alloy materials such as, but not limited to cobalt-chromium or stainless steel. These alloys provide the desired characteristics, such as flexibility and rigidity, to the stent. However, these alloys are not dense enough to be visible during the interventional process by current imaging methods such as fluoroscopy. To increase the radiopacity of the stents, and in an additional processing step, a radiopaque material is often welded to the stent after the stent is manufactured.

Accordingly, it would be desirable to build a medical device such as a stent by an additive manufacturing process with connectors between portions of the medical device that can be more easily, efficiently, and effectively removed without adversely affecting the remaining medical device. It would also be desirable to impart portions of a medical device with increased radiopacity in the same process.

BRIEF SUMMARY OF THE INVENTION

Embodiments hereof relate to a method of making a medical device using micro-cladding. The method includes forming a precursor medical device comprising a plurality of bands made of a first material disposed adjacent to each other, wherein each band is attached to an adjacent band by a plurality of first connectors configured to remain and a plurality of second connectors configured to be removed. The plurality of second connectors are made by functionally grading the first material with a second material to create embrittlement in the plurality of second connectors. The method further includes processing the precursor medical device to remove the plurality of second connectors without adversely affecting the bands and the plurality of first connectors.

Embodiments hereof also to a method of forming a medical device with radiopaque portions. The precursor medical device comprises forming a precursor medical device using micro-cladding, wherein the precursor medical comprises a plurality of bands made of a first material disposed adjacent to each other, wherein each band is attached to an adjacent band by a plurality of first connectors configured to remain and a plurality of second connectors configured to be removed. At least a portion of at least one of the plurality of bands and/or at least one of the plurality of first connectors is made radiopaque by functionally grading the first material with a second, radiopaque material. The method further includes processing the precursor medical device to remove the plurality of second connectors without adversely affecting the bands and the plurality of first connectors.

Embodiments hereof also relate to a precursor medical including a plurality of portion or bands made of a first material disposed adjacent to each other, a plurality of first connectors connecting each band to an adjacent band, and a plurality of second connectors connecting each band to an adjacent band. The plurality of first connectors are configured to remain and the plurality of second connectors are made by functionally grading the first material with a second material to create embrittlement such that the second plurality of connectors are configured to be removed.

Embodiments hereof also relate to a medical device including a plurality of portions or bands made of a first material disposed adjacent to each other and at least one connector connecting each band to an adjacent band. The at least one connector is made by functionally grading the first material with a second, radiopaque material.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements.

Figure 1:
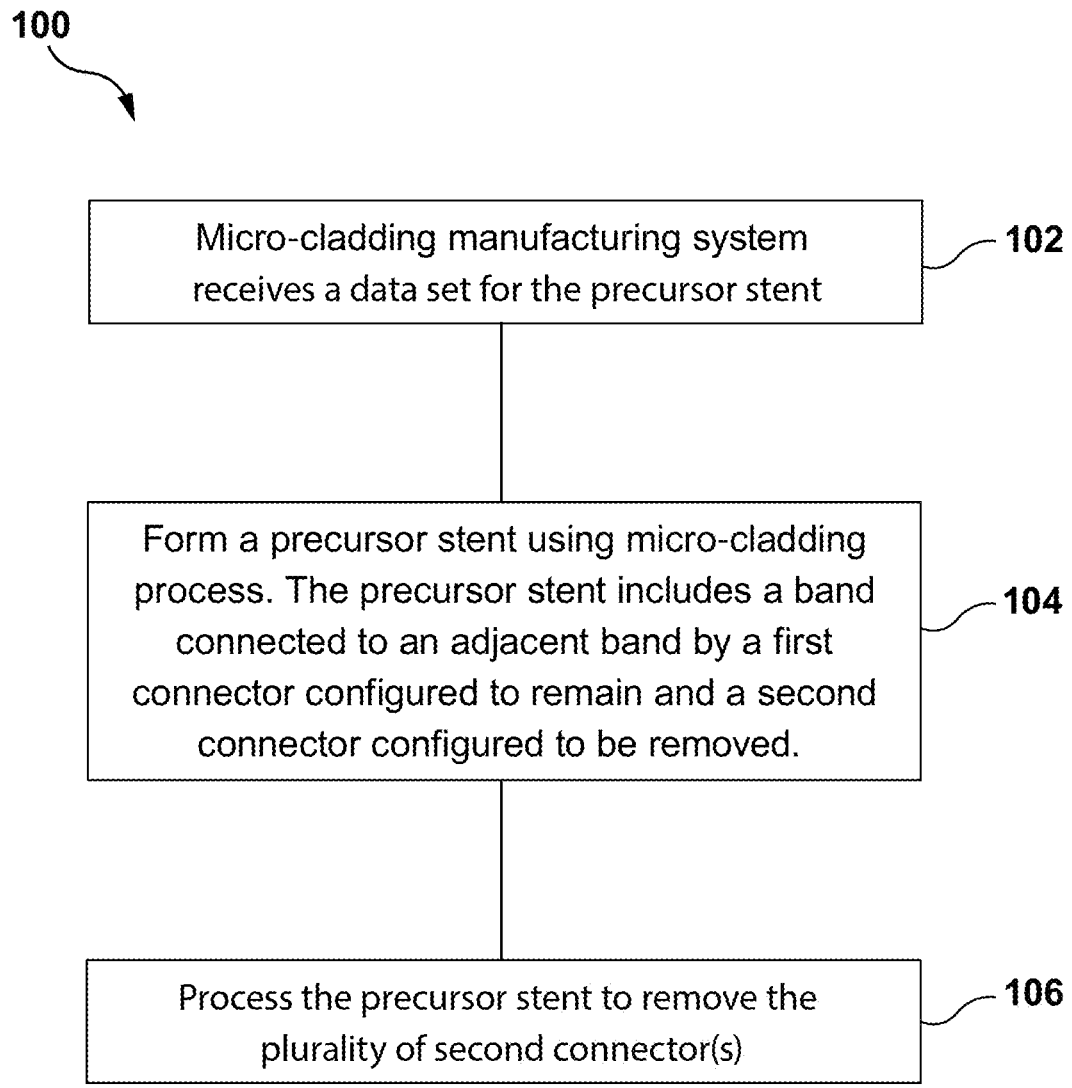
FIG. 1 is a flow chart showing steps in a method of making a medical device according to an embodiment hereof.

FIG. 1 is a flow chart showing an embodiment of a method 100 of forming a medical device according to an embodiment hereof. The method as described with respect to FIG. 1 is a method for making a medical device using laser micro-cladding, generally known as micro-cladding. Micro-cladding is a "laser metal deposition (LMD)" additive manufacturing process. The term "micro-cladding", also known generally as "additive manufacturing", "three-dimensional printing" or "rapid prototyping" refers to a process of making a three-dimensional solid object of virtually any shape from a digital model. Micro-cladding is achieved using an additive process, where successive layers of material are laid down in different shapes. The terms, as used herein, may refer to methods including, but not limited to laser metal deposition (LMD), laser cladding, and laser micro-cladding. Further, any type of additive manufacturing machine that can layer or clad the materials described herein may be used.

In general, micro-cladding makes parts by adding material instead of removing it. Laser additive manufacturing (LAM) is the process of using a laser to join materials to make structures. LAM is normally accomplished sequentially, layer by layer, using the information contained in 3D CAD files. LAM is generally divided into two categories: selective laser melting (SLM) or laser metal deposition (LMD). Laser Metal Deposition (LMD), also known as laser cladding, is the projection of metal powder melted in-flight using a high power energy beam such as a laser, and deposited on a substrate. The metal powder, requisite shielding gas, and energy beam may be simultaneously delivered, creating a melt pool on the substrate (work surface). Laser metal deposition (LMD) results in a full metallurgical bond between a layered, or clad material and the existing substrate. Laser micro-cladding is a sub-category of laser cladding and refers to the process as described above to fabricate miniaturized structures and components, such as certain types of medical devices.

Figure 2:
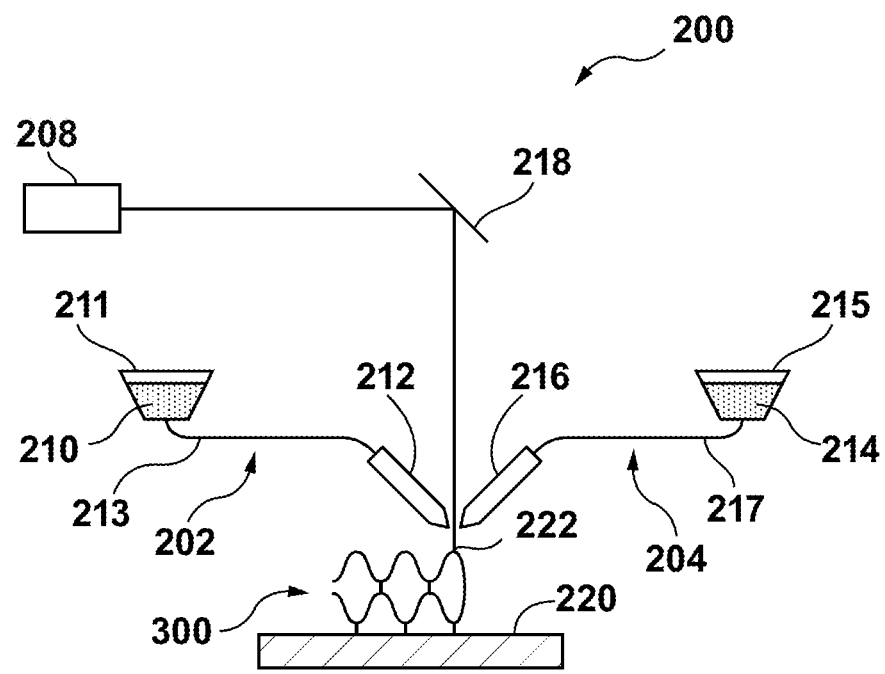
FIG. 2 is a schematic illustration of an embodiment of a micro-cladding system suitable for use with the method of FIG. 1.

Accordingly, FIG. 2 shows a simplified exemplary embodiment of a micro-cladding system 200 suitable for the purposes described herein. The micro-cladding system 200 of FIG. 2 includes a first powder delivery system 202, a second powder delivery system 204, a substrate 220, and an energy source or laser 208. The first powder delivery system 202 includes a first hopper 211, a first feed tube 213, and a first nozzle 212. The second powder delivery system 204 includes a second hopper 215, a second feed tube 217, and a second nozzle 216. In general, a first powder material 210 is dispensed from the first hopper 211 through the first feed tube 213 and the first nozzle 212. Similarly, a second powder material 214 is dispensed from the second hopper 215 through the second feed tube 217 and the second nozzle 216. The energy source 208, or laser, is targeted by a mirror 218 to creating a melt pool on the substrate 220 and selectively bond the first powder material 210 and/or the second powder material 212 at a fusion zone or laser focal zone 222 in a desired pattern. The substrate 220 is movable in three planes. The substrate 220 is retracted in a first direction Y1 and then moved in directions X1, X2, Z1, and Z2 such that successive layers of distributed first powder material 210 and/or second powder material 214 are deposited thereon and bonded until a desired object, in this example a precursor stent 300, is formed. The first powder material 210 may be materials conventionally used as materials for stent. For example, and not by way of limitation, the first powder material 210 may be stainless steel (e.g. SS316L), cobalt-chromium alloys, nickel titanium alloys (e.g. NITINOL), magnesium and magnesium alloys, or combinations thereof. The term "cobalt-chromium" alloys as used herein includes alloys with cobalt and chromium. Generally, materials such as, but not limited to, cobalt-nickel-chromium alloys (e.g. MP35N, MP20N, and MP35NLT) and chromium-nickel-tungsten-cobalt alloys ("L605") are the types of materials included in the term "cobalt-chromium alloys" as used herein. The second powder material 214 may be materials to modify characteristics of portions of a precursor stent, as described in more detail below. Specific embodiments of material that can be used as the second powder material 214 are described in more detail below.

The layered, or cladded bonding of the first and/or second powder materials 210, 214 requires an underlying support for the material to be bonded. Typically, after the first layer of material is deposited on the substrate 220, support is provided by the preceding bonded material. However, with certain medical devices, such as stents, it is desirable for a significant portion of a perimeter of a first band (portion) of the stent to not be connected to a second band (portion) of the stent. However, in many embodiments, these connecting portions cannot be excluded during additive manufacturing because the following layers need support upon which to build. Thus, when building such a stent vertically, it is desirable for connectors to be built between most or all of the crowns of adjacent bands in order to provide a support for the following layer of material. The micro-cladding system 200 of FIG. 2 is provided for exemplary purposes only and not meant to limit the invention. Other micro-cladding systems are possible including, but not limited to micro-cladding systems with more or fewer powder delivery systems and systems wherein the energy source is directed through the nozzles of the system.

Figure 3:
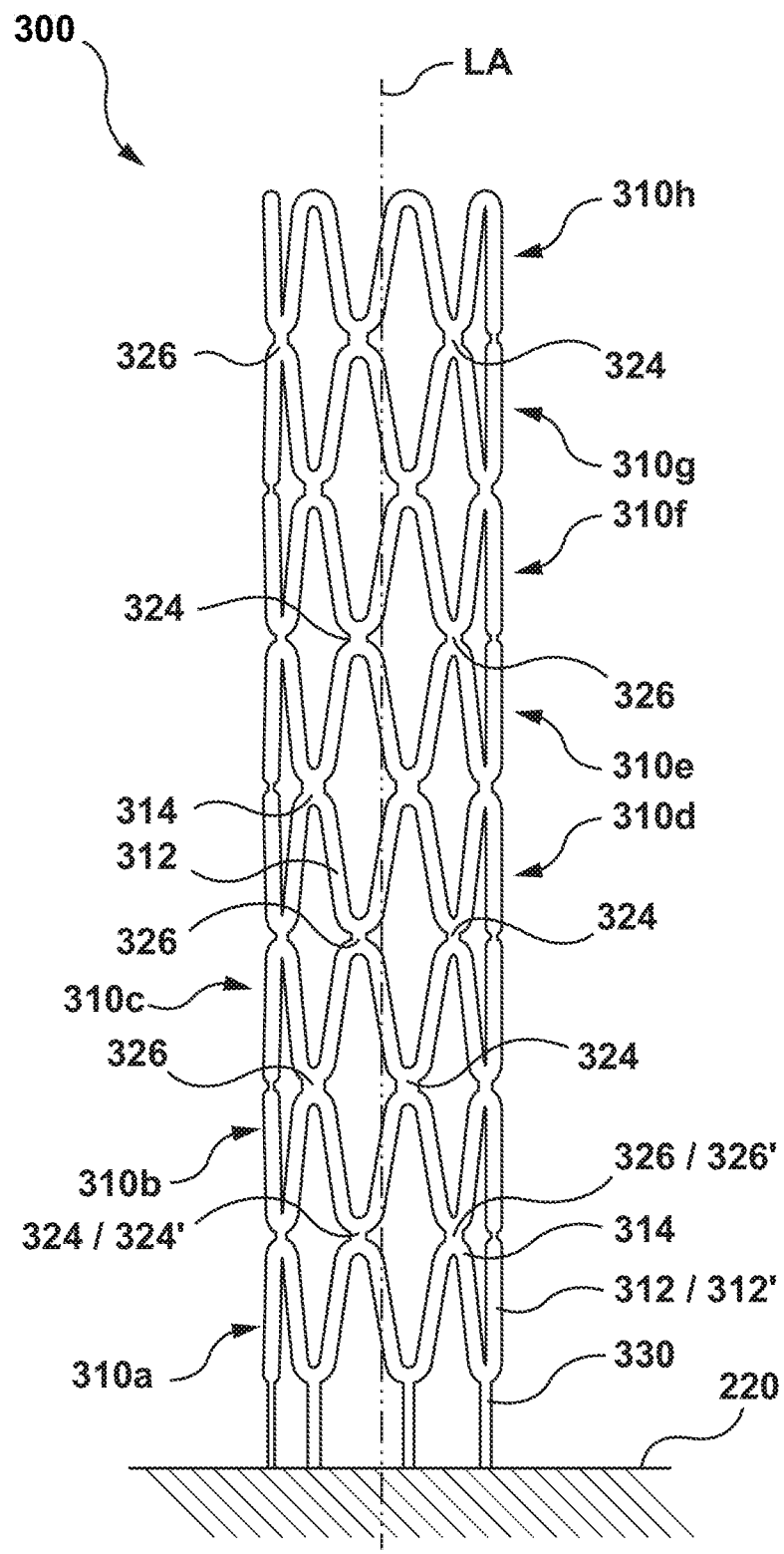
FIG. 3 is a schematic side illustration of an embodiment of a precursor stent made in a step of the method of FIG. 1.

The method of FIG. 1 using the micro-cladding system 200 such as described with respect to FIG. 2 will now be described in greater detail. In this description, the method of FIG. 1 will be described with respect to forming a stent. However, it is understood that other similar medical devices may be formed using the method of FIG. 1. In an embodiment, in step 102 of FIG. 1, the micro-cladding system 200 receives a dataset corresponding to a medical device such as a precursor stent 300, as shown in FIG. 3. In particular, the dataset is information regarding the characteristics of the precursor stent 300 from which the micro-cladding system 200 can form the precursor stent 300. For example, the sizes and locations of parts of the precursor stent 300 may be part of the dataset such that the micro-cladding system 200 can form the precursor stent 300. For example, and not by way of limitation, the dataset may be a 3D printable file such as an STL file. STL (STereoLithography) is a file format native to the stereolithography CAD software created by 3D Systems. STL is also known as Standard Triangle Language and Standard Tessellation Language. This file format is supported by many software packages for use with additive manufacturing.

In step 104 of the method of FIG. 1, the micro-cladding system 200 forms the precursor stent 300, as shown in FIG. 3. In step 104, the micro-cladding system 200 lays down successive layers or clads of a powder or powders of the desired materials to build the precursor stent 300 from a series of cross sections. FIG. 3 shows an embodiment of the precursor stent 300. According to an embodiment hereof, the precursor stent 300 is built by micro-cladding such that the precursor stent 300 is built vertically on the substrate 220. The substrate 220 may be any material suitable to be used in the environment of and with the materials used for the micro-cladding manufacturing process. In the embodiment shown, the precursor stent 300 includes a plurality of ring-shaped elements or bands 310 formed of a first material. The bands 310 may also be referred to as cylindrical elements or portions. In the embodiment of FIG. 3, the precursor stent 300 includes eight bands 310a-310h, however, more or fewer bands 310 may be utilized. Each band 310 is disposed adjacent to another band 310 along a longitudinal axis LA to form a tube or cylinder. Each band 310 is a waveform formed from a plurality of struts 312 connected together by bends or crowns 314. Further, the crowns 314 of the adjacent bands 310 are connected to each other by at least one first connector 324 and a plurality of second connectors 326. Further, in an embodiment, the first band 310 may be separated from the substrate 220 by stilts or connectors 330, as shown in FIG. 3, which may also be built by the micro-cladding manufacturing process.

Further, in some embodiments, it may be desirable for portions of the precursor stent to be radiopaque. Therefore, in some embodiments, step 104 includes making portions of the precursor stent 300 radiopaque, as will be described in more detail below. The term "radiopaque" refers to the ability of a substance to absorb X-rays. Few substances will transmit 100% of X-rays and few substances will absorb 100% of X-rays. For the purposes of this disclosure, "radiopaque" will refer to those substances or materials which have suitable visibility for stent procedures when being imaged by an X-ray imaging device such as but not limited to a fluoroscope.

The first connectors 324 and the second connectors 326 are distinguished from each other in that the first connectors 324 are configured to remain connecting the adjacent crowns 314 to each other, while the second connectors 326 are configured to be removable from the precursor stent 300. Similarly, the stilts 330 are configured to be removable from the precursor stent 300 such that the band 310a closest to the substrate 220 is not damaged when separating the precursor stent 300 from the substrate 220. Although a particular precursor stent 300 embodiment is shown in FIG. 3, different precursor stents may be formed using the micro-cladding manufacturing process. For example, and not by way of limitation, additional connectors may be utilized, the bands may be slanted, different bands may have different features (such as different thicknesses), additional features such as surface features, notches, etc. may be added, and other stent design differences may be utilized which are capable of being made using the micro-cladding manufacturing process.

As explained above, each crown 314 of a band 310 is connected to a corresponding crown 314 of an adjacent band 310 by a first connector 324 or a second connector 326. However, as also explained above, for certain applications it would be desirable for some of the crowns 314 of a band 310 to be independent or not connected to the corresponding crown 314 of an adjacent band 310. As also explained above, the second connectors 326 cannot simply be excluded from the precursor stent 300 when forming the precursor stent 300 by micro-cladding because excluding such second connectors 326 when building a precursor stent vertically on the substrate 220 would result in instability between the adjacent bands 310 during the micro-cladding manufacturing process. For example, and not by way of limitation, if only one first connector 324 were included between the first band 310a and the second band 310b of FIG. 3, the second band 310b would tend to move towards the first band 310a at the crowns 314 without a connector due to gravity. Such a tendency would negatively impact the ability to build a stent with the desired characteristics.

Accordingly, step 106 of the method 100 of FIG. 1 is to process the precursor stent 300 to remove the plurality of second connectors 326 between crowns 314 of adjacent bands 310. In the particular embodiment of FIG. 3, the second connectors 326 are selected to be removed such that only a single first connector 324 is disposed between each band 310 and its adjacent band 310. However, the number and type of second connectors 326 to be removed can be selected depending on various factors including, but not limited to, the desired flexibility of the resulting stent.

As explained above, it is desirable to minimize difficulty in removing the second connectors. Therefore, in embodiments of the present application, the second connectors 326 are formed by either abruptly transitioning from the first material to the second material or by functionally grading a first material and a second material such that the second connectors 326 are more brittle than the first connectors 324 and the bands 310 of the precursor stent 300. Similarly, the stilts 330 may be formed by similar methods. With the second connectors 326 and the stilts 330 more brittle than the bands 310 and the first connectors 324, the second connectors 326 and the stilts 330 may be easily removed by mechanical, chemical, or other suitable methods.

Functional grading is the variation in structure of two materials over a volume. Stated more plainly, functional grading is changing the ratio or mix of the first material to the second material. Functional grading results in corresponding changes in the properties of the final material. Therefore, specific properties may be imparted on specific areas of structures formed by the micro-cladding manufacturing process using functional grading. For example, and not by way of limitation, functional grading may be utilized to increase strength, rigidity, radiopacity, embrittlement, or corrosion resistance over the first, or base material or alloy. As an example, in the embodiment of the method of FIG. 1, it would be desirable to embrittle, or make more brittle the second connectors 326 of the precursor stent 300 such that the second connectors 326 may be easily removed from the precursor stent 300 during the processing of step 106. Therefore, each second connector 326 may be embrittled by functional grading such that each second connector 326 may be easily removed without adversely affecting the bands 310 and the plurality of first connectors 324. Provided below are embodiments of materials and methods to make the second connectors 326 brittle and embodiments to make portions of the precursor stent 300 radiopaque.

Figure 6:
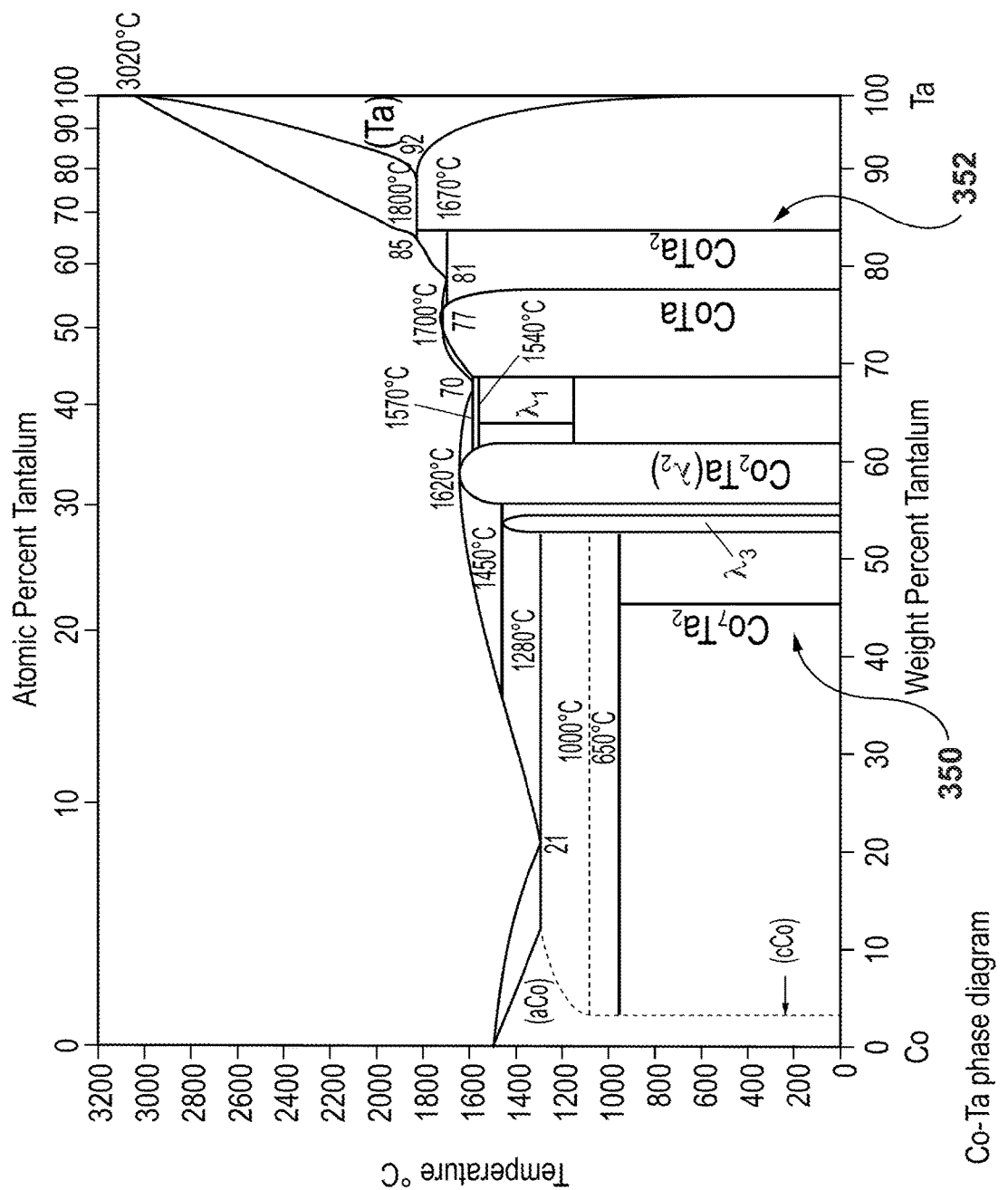
FIG. 6 is a chart illustrating a phase diagram of the system of the functional grading profile of FIG. 5.

In the examples explained below, cobalt is used as the first powder material 210 and tantalum is used as the second powder material 214. However, this is not meant to be limiting. Cobalt is used in the examples as the first powder material 210 because cobalt is the primary metal in cobalt-chromium alloys, such as MP35N. However, as would be understood by those skilled in the art the properties of MP35N are not identical to cobalt. Further, tantalum is used in the examples as the second powder material 214 because it is an example of a radiopaque material used in medical devices. Further, cobalt and tantalum are used in the examples due to the cobalt-tantalum phase diagram (FIG. 6). As would be understood by those skilled in the art, the principles explained below can be used with other materials, such as those listed above and below. With the materials selected as the first powder material 210 and the second powder materials 214, a phase diagram of the two materials selected, similar to the phase diagram in FIG. 6 for cobalt-tantalum, may be referenced to utilize the principles discussed below to functionally grade the two materials for embrittlement and/or radiopacity, as described in more detail below.

Figure 4:
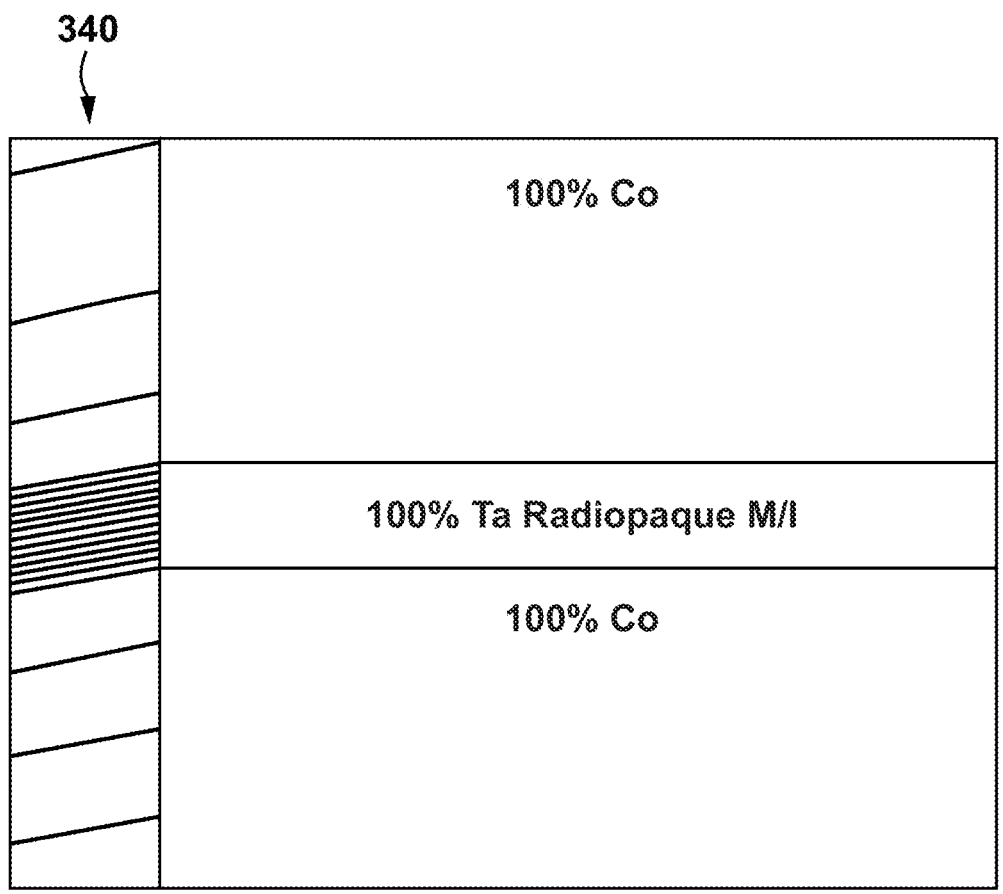
FIG. 4 is a chart illustrating an example of an abrupt transition functional grading profile of a second connector of the precursor stent of FIG. 3.

In an example for making the second connectors 326 easy to remove, the first powder material 210 is cobalt or a cobalt alloy, as described above. The second powder material 214 is tantalum. The bands 310 and the first connectors 324 of the precursor stent 300 are formed of the first powder material 210. In an example, the plurality of second connectors 326 of FIG. 3 are formed by abruptly transitioning from the first powder material 210 to the second powder material 214. Thus, as the substrate 220 of the micro-cladding system 200 is moved to form layers of the bands 310 and the first connectors 324, the first powder material 210 is dispensed from the first hopper 211. When a layer of one of the second connectors 326 is to be formed, the second powder material 214 is dispensed from the second hopper 215. This is an abrupt or stepwise transition from the first powder material 210 to the second powder material 214, as shown in the transition profile chart of FIG. 4. The hash marks 340 of FIG. 4 indicate the relative level of the first material (cobalt or cobalt alloy) and the second material (tantalum). Thus, in the example of FIG. 4, hash marks 340 that are spaced apart are the first material (cobalt) and hash marks that are close together are the second material (tantalum). The abrupt transition from 100% cobalt to 100% tantalum causes embrittlement in that area. Similarly, the abrupt transition from 100% tantalum back to 100% cobalt causes embrittlement in that area. In an embodiment, these transition areas are at the transition from the crowns 314 to the second connectors 326, as shown in FIG. 4. Thus, the connection between the second connectors 326 and the adjacent crowns 314 is brittle, making the connection easy to break. Thus, the second connectors 326 may be removed mechanically by breaking the connection between the second connectors 326 and the adjacent crowns 314. Further, because the second connectors 326 in this example do not include any of the first powder material 210, the second connectors 326 may be removed by other methods such a chemical etching, as described in U.S. Pat. No. 9,114,032 assigned to Medtronic Vascular, Inc. and incorporated by reference herein in its entirety. The stilts 330 may be formed in the same manner for easy removal from the first band 310a.

Figure 5:
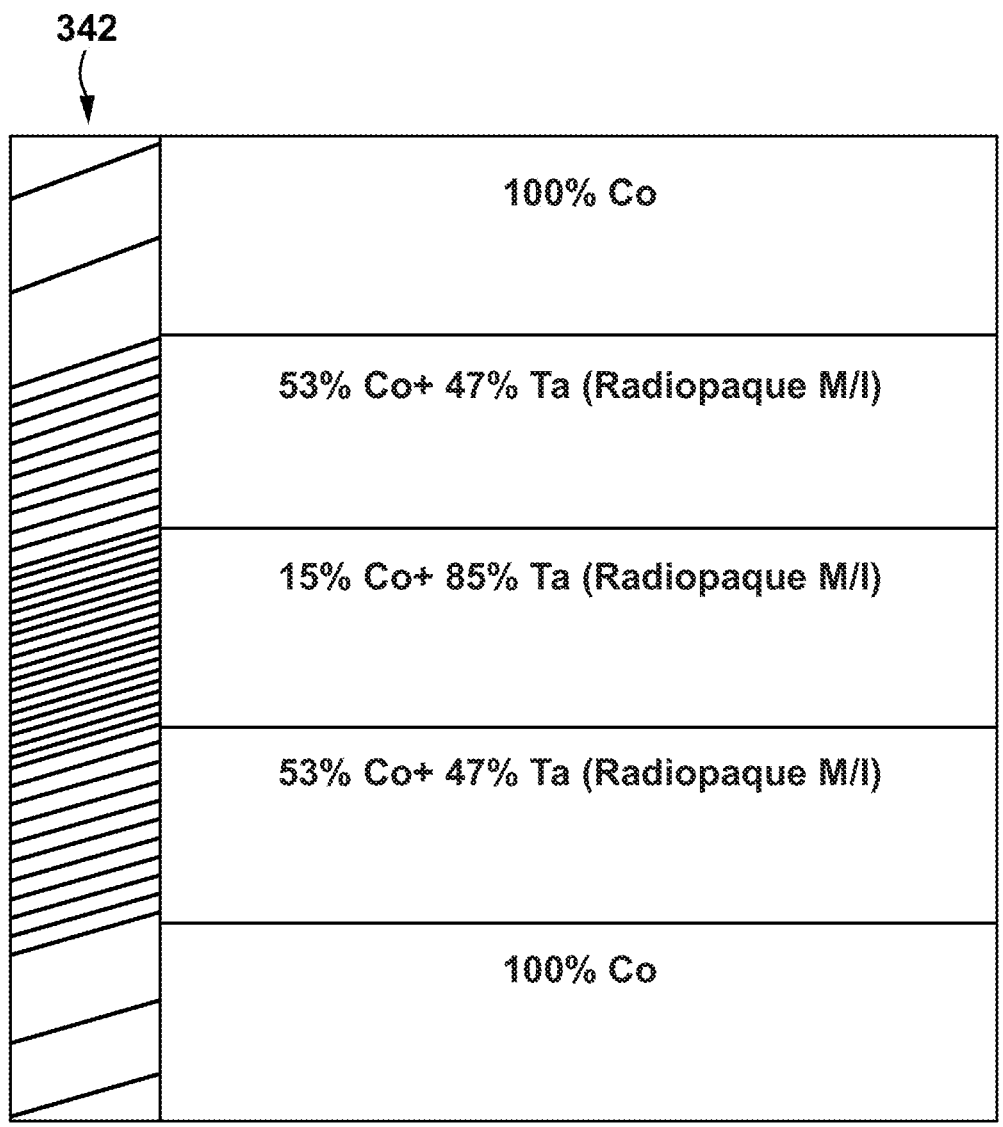
FIG. 5 is a chart illustrating another example of a functional grading profile of a second connector of the precursor stent of FIG. 3.

In another example shown in FIG. 5, the plurality of second connectors 326' are embrittled by forming each second connector 326' by functionally grading the first powder material 210 and the second powder material 214 to form detrimental second phase intermetallic compounds. By "detrimental second phase intermetallic compounds", it is meant that the second phase intermetallic compounds of sufficient size and quantity to embrittle each second connector 326'. Such detrimental intermetallic compounds are larger than nano-sized. Second phase intermetallic compounds are crystal structures of an intermediate phase, formed through functionally grading the first material and the second material in specific ratios at specific temperature ranges. Second phase intermetallic compounds are different from either base material. They include fixed composition and are similar to alloys, however the bonding between the different atoms of a second phase intermetallic compound is partly ionic. This leads to different properties and characteristics than traditional alloys. Thus, second phase intermetallic compounds have their own crystal structure and are almost always brittle.

In the example shown in FIG. 5, the first powder material 210 is cobalt and the second powder material 214 is tantalum. As with the embodiment described above, the bands 310, including the struts 312 and crowns 314, the first connectors 324, and the second connectors 326' may be formed by using the micro-cladding system 200. As the substrate 220 is moved to form layers of the bands 310 and the first connectors 324, the first powder material 210 is dispensed from the first hopper 211. At locations of the second connectors 326', both the first powder material 210 and the second powder material 214 are dispensed in the ratios shown in FIG. 5. Thus, in the example, the crown 314 adjacent the second connector 326' is 100% cobalt. The initial layers of each second connector 326' are formed with 53% cobalt and 47% tantalum as shown in FIG. 5. Then, the middle portion of each second connector 326' is formed with 15% cobalt and 85% tantalum, as also shown in FIG. 5. Then, the end portion adjacent to another crown 314 is formed with 53% cobalt and 47% tantalum, as shown in FIG. 5.

FIG. 6 is a cobalt-tantalum phase diagram. As can be seen at 350, using 53% cobalt and 47% tantalum under certain conditions forms a second phase intermetallic $Co_7Ta_2$. Similarly, as shown at 351, using 15% cobalt and 85% tantalum under certain conditions forms a second phase metallic $CoTa_2$. Each of these second phase intermetallic compounds is hard and brittle. Thus, each second connector 326' is made brittle by forming each second connector 326' from combinations of the first powder material 210 and the second powder material 214 to form two detrimental second phase intermetallic compounds as shown in the transition profile of FIG. 5. Alternatively, each second connector 326' may be formed of only one detrimental second phase intermetallic compound. The hash marks 342 to the left of the functional grading ratios in the transition profile of FIG. 5 indicate the relative ratio of cobalt and tantalum. Hash marks 342 that are spaced apart are mostly or all cobalt and as the hash marks 342 move closer together, the ratio of tantalum increases relative to cobalt.

As explained above, step 106 of the method 100 of FIG. 1 is to process the precursor stent 300 to remove the plurality of second connectors 326 between the crowns 314 of the adjacent bands 310 and the plurality of stilts 330 without adversely affecting the adjacent bands 310 and the plurality of first connectors 324. In the example of the second connector 326 of FIG. 4, wherein the second connectors 326 are formed by abrupt material transitions, the plurality of second connectors 326 may be removed by methods such as, but not limited to chemical dissolution or chemical etching. However, in the example of FIGS. 5-6, wherein the second connectors 326' are made brittle by functional grading to form detrimental second phase intermetallic compounds, the second connectors 326' may be removed by mechanical methods such as, but not limited to laser ablation, electrical discharge machining (EDM), water jet, electron beam, focused ion beam (FIB), micromachining, and other similar methods. Additionally, the stilts 330 may be removed by methods similar to the methods for removing the second connectors 326, 326'.

As described previously, some materials generally used for stents are not radiopaque. Thus, radiopaque bands or other radiopaque devices are sometimes added to stents to aid in visually detecting the stent. In an embodiment of the present application, functional grading of the first powder material 210 and the second powder material 214 may be used to impart radiopacity on portions of a medical device such as a stent. In particular, functional grading may be used to add radiopacity to portions of the precursor stent 300 configured to remain. In some embodiments, radiopacity may be added to low-stress components of the precursor stent 300, such as the struts 312 and/or the plurality of first connectors 324 using functional grading.

Figure 7:
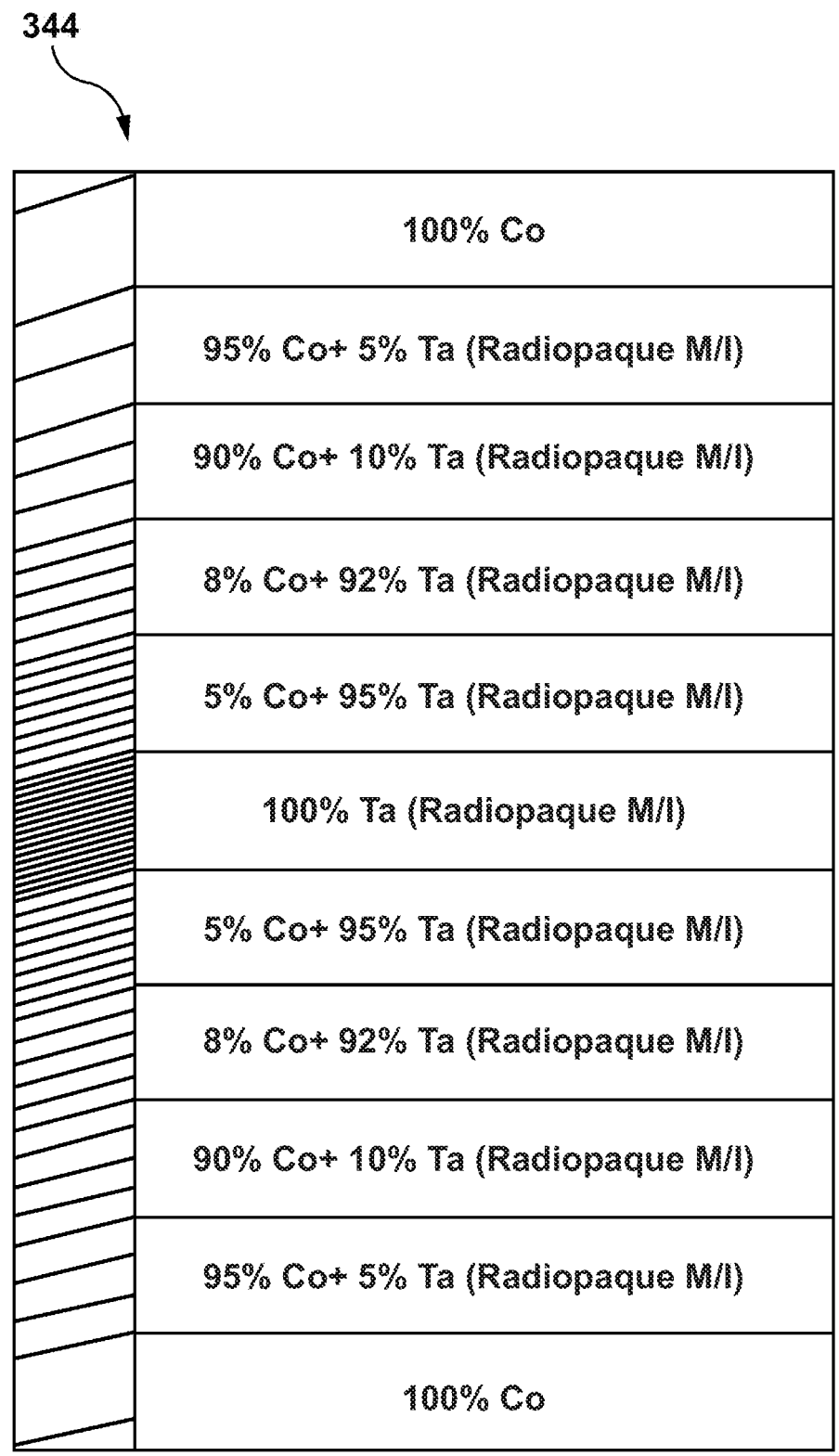
FIG. 7 is a chart illustrating an example of a functional grading profile of a first connector of the precursor stent of FIG. 3.

In an example, the plurality of first connectors 324' are made radiopaque by functionally grading a first powder material 210, cobalt, with a radiopaque second powder material 214, tantalum, in a transition profile as shown in FIG. 7. In the example of FIG. 7, the functional grading is performed to minimize the formation of second phases of cobalt-tantalum described above (i.e., minimize the formation of $Co_7Ta_2$, $Co_6Ta_7$, $CoTa_2$). By minimizing the formation of second phase intermetallic compounds, it is meant that the second phase intermetallic compounds are of sufficiently small quantity and size (nano-sized or smaller) to not cause embrittlement. Thus, the plurality of first connectors 324' may be made radiopaque without being made brittle. In the embodiment shown in FIG. 7, each first connector 324' adjacent to a corresponding crown 314 of a corresponding band 310 is generally 100% cobalt. As each first connector 324' is formed layer by layer by the micro-cladding manufacturing process, the ratio of the second powder material 214 to the first powder material 210 is increased. In the example of FIG. 7, a middle portion of the first connector 324' is 100% tantalum. As the first connecter 324' is formed such that the layers move away from the middle portion toward a corresponding crown 314 of an adjacent band 310, the ratio of the second powder material 214 to the first powder material 210 is decreased such that adjacent the corresponding crown 314 of the adjacent band 310, first connector is 100% of the first powder material (cobalt). The hash marks 344 to the left of the functional grading profile ratios in FIG. 7 indicate the ratio of the first material and the second material, and also the radiopacity of the material compound in comparison to the radiopacity of the first material. Thus, the hash marks 344 spaced far apart are 100% of the first material (Cobalt) and the resulting material is not radiopaque. As the hash marks 344 move closer together, the ratio of the second material increases and the ratio of the first material decreases. Further, as the hash marks move closer together, radiopacity of the resulting material increases.

Figure 8:
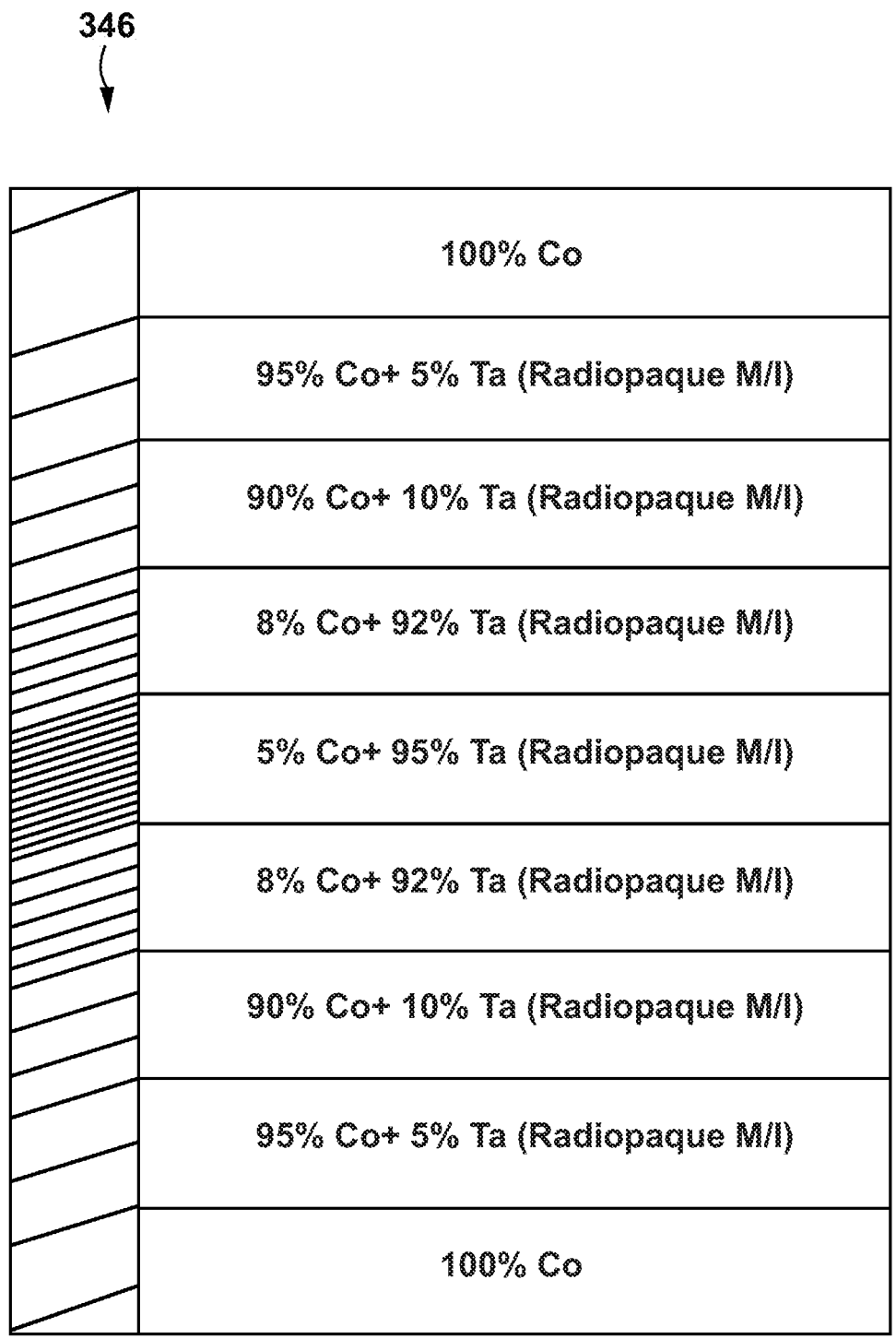
FIG. 8 is a chart illustrating an example of a functional grading profile of a strut of the precursor stent of FIG. 3.

FIG. 8 shows another example of functional grading that can be used at the plurality of first connectors 324' configured to remain such that the first connectors 324' are radiopaque. As with the embodiment of FIG. 7, the functional grading is performed to minimize the formation of second phases of the first and second materials, in this case cobalt and tantalum (i.e., minimize the formation of $Co_7Ta_2$, $Co_6Ta_7$, $CoTa_2$). Thus, the plurality of first connectors 324' may be made radiopaque without being made brittle. In the embodiment shown in FIG. 8, each first connector 324' adjacent to a corresponding crown 314 of a corresponding band 310 is generally 100% cobalt. As each first connector 324' is formed layer by layer by the micro-cladding manufacturing process, the ratio of the second powder material 214 to the first powder material 210 is increased. In the example of FIG. 7, a middle portion of the first connector 324' is about 5% cobalt and 95% tantalum. As the first connecter 324' is formed such that the layers move away from the middle portion toward a corresponding crown 314 of an adjacent band 310, the ratio of the second powder material 214 to the first powder material 210 is decreased such that adjacent the corresponding crown 314 of the adjacent band 310, the first connector is 100% of the first powder material (cobalt). The hash marks 346 to the left of the functional grading profile ratios in FIG. 8 indicate the ratio of the first material and the second material, and also the radiopacity of the material compound in comparison to the radiopacity of the first material. Thus, the hash marks 346 spaced far apart are 100% of the first material (Cobalt) and the resulting material is not radiopaque. As the hash marks 346 move closer together, the ratio of the second material increases and the ratio of the first material decreases. Further, as the hash marks move closer together, radiopacity of the resulting material increases.

Figure 9:
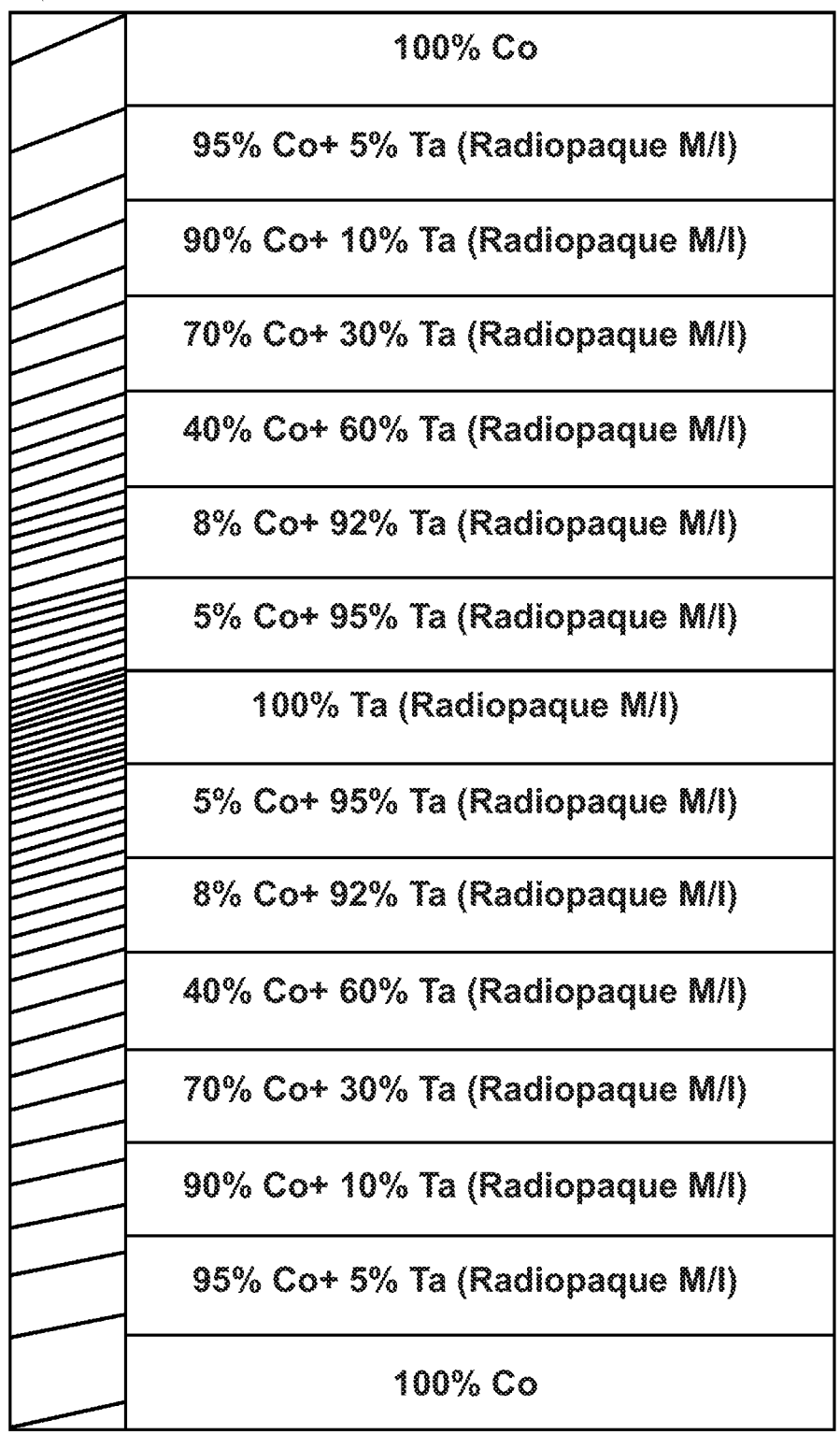
FIG. 9 is a schematic illustration of a flattened, two-dimensional representation of a portion of a band of the precursor stent of FIG. 3.

FIG. 9 shows another example of functional grading that can be used at the plurality of first connectors 324' configured to remain such that the first connectors 324' are radiopaque. As with the embodiment of FIGS. 7 and 8, the functional grading is performed to minimize the formation of second phases of the first and second materials, in this case cobalt and tantalum (i.e., minimize the formation of $Co_7Ta_2$, $Co_6Ta_7$, $CoTa_2$). Thus, the plurality of first connectors 324' may be made radiopaque without being made brittle. In the embodiment shown in FIG. 9, each first connector 324' adjacent to a corresponding crown 314 of a corresponding band 310 is generally 100% cobalt. As each first connector 324' is formed layer by layer by the micro-cladding manufacturing process, the ratio of the second powder material 214 to the first powder material 210 is increased. In the example of FIG. 9, a middle portion of the first connector 324' is about 100% tantalum. As the first connecter 324' is formed such that the layers move away from the middle portion toward a corresponding crown 314 of an adjacent band 310, the ratio of the second powder material 214 to the first powder material 210 is decreased such that adjacent the corresponding crown 314 of the adjacent band 310, the first connector is 100% of the first powder material (cobalt). The embodiment of FIG. 9 is generally similar to the embodiment of FIG. 7 except that the transition from 100% of the first material (cobalt) to 100% of the second material (tantalum) is more gradual. The hash marks 348 to the left of the functional grading profile ratios in FIG. 9 indicate the ratio of the first material and the second material, and also the radiopacity of the material compound in comparison to the radiopacity of the first material. Thus, the hash marks 348 spaced far apart are 100% of the first material (Cobalt) and the resulting material is not radiopaque. As the hash marks 348 move closer together, the ratio of the second material increases and the ratio of the first material decreases. Further, as the hash marks move closer together, radiopacity of the resulting material increases.

Figure 10:
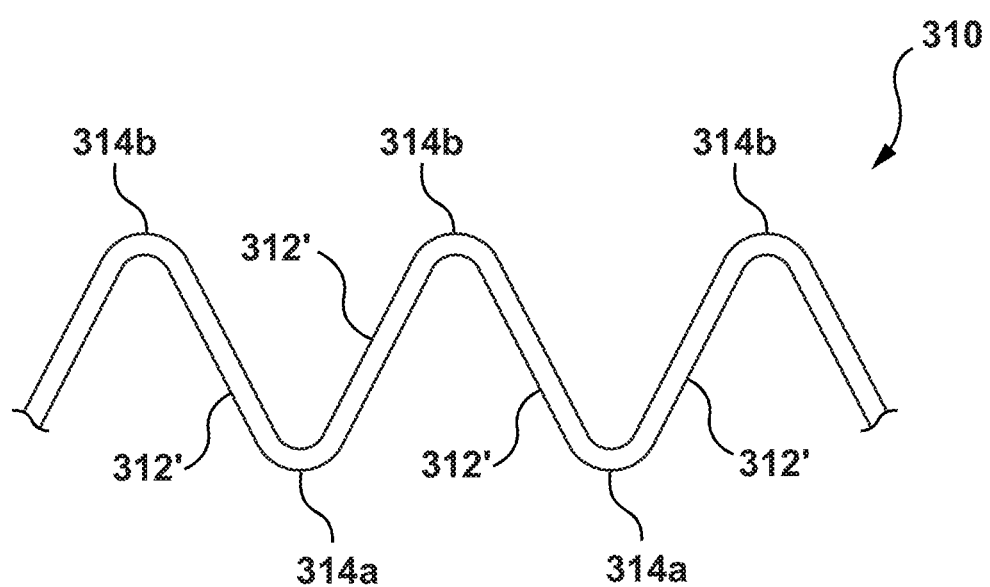
FIG. 10 is a chart illustrating yet another example of a functional grading profile of the first connectors and/or the struts of the precursor stent of FIG. 3.

The embodiments of FIGS. 7-9 have been described with respect to making radiopaque at least some of the plurality of first connectors 324' configured to remain. However, these embodiments are not limited to the plurality of first connectors. In other embodiments, other portions of the precursor stent 300 that are configured to remain may be made radiopaque. For example, as shown in FIG. 10, at least some of the struts 312' of the precursor stent 300 may be radiopaque in the same manner described above with respect to FIGS. 7-9. FIG. 10 shows an example band 310 in flattened for simplified viewing. The example band 310 can be any or all of the bands 310 of FIG. 3. In some instances, it may be desirable for all or some of the struts 312' of some or all of the bands 310 to be radiopaque. For example, and not by way of limitation, it may desirable for the struts of the end bands (bands 310a and 310h) to be radiopaque such that the ends of the stent may be seen under fluoroscopy. In an embodiment to form the struts 312' to be radiopaque, referring to FIG. 10, as the substrate 220 moves such that the crowns 314a are being formed, the first powder material 210 is deposited on a previous layer and fused by the laser 208. This occurs for each layer of the crowns 314a. As the layers are being built upon one another and the struts 312' are beginning to be formed, the second powder material 214 is gradually added and the amount of the first powder material 210 is gradually decreased to form layers of the struts 312'. The gradual increase/decrease can be according to any of the embodiments of FIGS. 7-9. Upon reaching approximately the center of each strut 312', the amount of second powder material 214 is decreased and the amount of the first powder material 210 is increased for layers towards the crowns 314b until the layers at the crowns 314b are 100% the first powder material. This gradual decrease/increase may also be according to the embodiments of FIGS. 7-9. The resulting struts 312' are radiopaque without detrimentally affecting the strength, rigidity and overall performance of the precursor stent 300.

Figure 11:
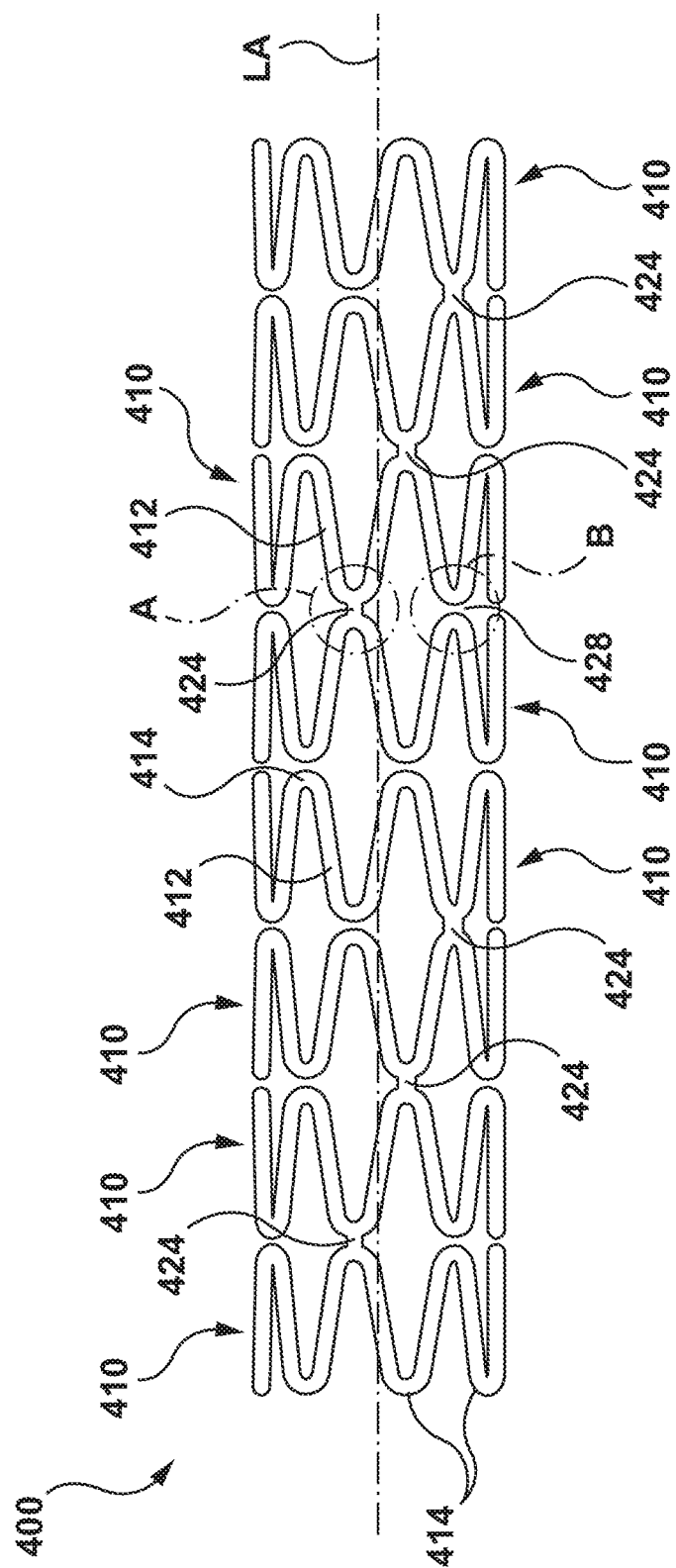
FIG. 11 is a schematic side illustration of an embodiment of a stent made using the method of FIGS. 1-10.
Figure 13:
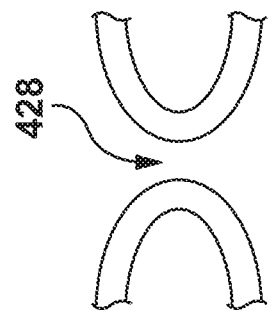
FIG. 13 is a close-up schematic illustration of an embodiment of a gap between crowns of adjacent bands of the stent of FIG. 11 taken at area "B" of FIG. 11.
Figure 12:
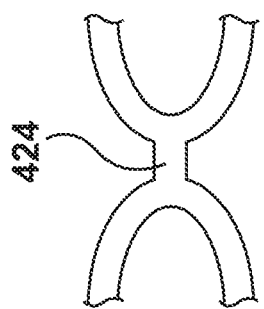
FIG. 12 is a close-up schematic illustration of an embodiment of a first connector between crowns of adjacent bands of the stent of FIG. 11 taken at area "A" of FIG. 11.

Discussed above were various embodiments for making the precursor stent 300. As also described above with respect to step 104 of the method of FIG. 1, the plurality of second connectors 326, 326' and the optional stilts 330 are removed from the precursor stent 300. With the plurality of second connectors 326, 326' and the stilts 330 removed, the precursor stent 300 becomes the stent 400 shown in FIGS. 11-13. The stent 400 includes a plurality of ring-shaped elements or portions or bands 410. In the embodiment of FIG. 11, the stent 400 includes eight bands 410 corresponding to the eight bands 310 of the precursor stent 300. However, more or fewer bands 410 may be utilized. Each band 410 is disposed adjacent to another band 410 along a central longitudinal axis LA to form a tube or cylinder. Each band 410 is a waveform formed from a plurality of struts 412 connected together by bends or crowns 414. At least one crown 414 of each band 410 is connected to a corresponding crown 414 of an adjacent band 410 by a first connector 424. FIG. 12 shows a close-up illustration of one first connector 424 connecting the crowns 414 of adjacent bands 410 to each other. At other crowns, a gap 428 is disposed between the crown 414 and the corresponding crown 414 of the adjacent bands 410, as shown in FIG. 13. It is understood that the stent 400 shown in FIGS. 11-13 may have radiopaque first connectors 424 if the methods used as described above were used to make first connectors 324' radiopaque. Similarly, at least some of the struts 412 of the stent 400 may be radiopaque if the methods used as described above were used to make the corresponding struts 312' of the precursor stent 300 radiopaque.

The specific embodiments described above for functionally grading a first material and a second material to make connectors brittle or to make connectors or struts radiopaque used cobalt and tantalum as the first and second materials, respectively. However, these are examples and other materials may be used in keeping with the present disclosure. For example, and not by way of limitation, the first material may be stainless steel and stainless steel alloys (e.g. SS316L), cobalt-chromium alloys, nickel titanium alloys (e.g. NITINOL), magnesium and magnesium alloys, or combinations thereof. The term "cobalt-chromium" alloys as used herein includes alloys with cobalt and chromium. Generally, materials such as, but not limited to, cobalt-nickel-chromium alloys (e.g. MP35N, MP20N, and MP35NLT) and chromium-nickel-tungsten-cobalt alloys ("L605") are the types of materials included in the term "cobalt-chromium alloys" as used herein. Further, the second material may be platinum, gold, tantalum, and other radiopaque materials known to those skilled in the art. Moreover, the exemplary functional grading ratio profiles and transition rates provided with the method of manufacturing the precursor stent 300 are examples only and are not meant to be limiting. Other functional grading systems, system ratio profiles and transition rates may be utilized based upon the application.

While the embodiments shown and described herein refer to a crown connected to a corresponding crown of an adjacent band on the precursor stent, other connections between adjacent bands may be used. For example, and not by way of limitation, a crown of one band may be connected to a strut of an adjacent band, or struts of adjacent bands may be connected. Further, the first connectors 324 and the second connectors 326 may be angled with respect to the longitudinal axis LA or may be curved.

Although the embodiments shown and described herein refer to a precursor stent with bands, at least one first connector, and a plurality of second connectors, the precursor stent processed to form a stent, this is not meant to limit the method, and other medical devices may be manufactured utilizing the method described herein.

Further, while various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of making a stent comprising the steps of: forming a precursor stent using micro-cladding, wherein the precursor stent comprises a plurality of bands made of a first material disposed adjacent to each other, wherein each band is attached to an adjacent band by a plurality of first connectors configured to remain and a plurality of second connectors configured to be removed, wherein the plurality of second connectors are made by functionally grading the first material with a second material to create embrittlement in the plurality of second connectors;
processing the precursor stent to remove the plurality of second connectors without adversely affecting the bands and the plurality of first connectors.

2. The method of claim 1, wherein the step of processing the precursor stent to remove the plurality of second connectors comprises mechanically removing the plurality of second connectors.

3. The method of claim 1, wherein the second material is a radiopaque material.

4. The method of claim 1, wherein the plurality of second connectors are made by creating abrupt transitions between the first material and the second material.

5. The method of claim 1, wherein the plurality of second connectors are made by functionally grading the first material and the second material to form detrimental second phase intermetallic compounds to impart embrittlement in the plurality of second connectors.

6. The method of claim 1, wherein first material is selected from the group consisting of a cobalt-chromium alloy and stainless steel, and the second material is selected from the group consisting of tantalum, platinum, and gold.

7. The method of claim 1, wherein at least one of the plurality of first connectors is made by functionally grading the first material and a third material, wherein the third material is a radiopaque material, such that the at least one of the plurality of first connectors is radiopaque.

8. The method of claim 7, wherein the step of functionally grading the first material and the third material for the at least one of the plurality of first connectors comprises gradually transitioning from a larger percentage of the first material to a larger percentage of the third material as layers of the at least one of the plurality of first connectors are added and then gradually transitioning back from a larger percentage of the third material to the first material as layers are added, such as to minimize the formation of second phase intermetallic compounds in the at least one of the plurality of first connectors.

9. The method of claim 7, wherein second material and the third material are the same material.

10. The method of claim 1, wherein a portion of at least one of the plurality of bands is formed by functionally grading the first material and a third material, wherein the third material is a radiopaque material, such that the portion of the at least one of the plurality of bands is radiopaque.

11. The method of claim 10, wherein the third material and the second material are the same material.

12. The method of claim 10, wherein the step of functionally grading the first material and the third material for the portion of the at least one of the plurality of bands comprises gradually transitioning from the first material to a larger percentage of the third material than the first material, and then gradually transitioning back from a larger percentage of the third material than the first material to the first material as layers are added, such as to minimize the formation of second phase intermetallic compounds in the at least one of the plurality of first connectors.

13. A method of making a stent comprising the steps of: forming a precursor stent using micro-cladding, wherein the precursor stent comprises a plurality of bands made of a first material disposed adjacent to each other, wherein each band is attached to an adjacent band by a plurality of first connectors configured to remain and a plurality of second connectors configured to be removed, wherein at least one of a portion of at least one of the plurality of bands or at least one of the plurality of first connectors is made radiopaque by functionally grading the first material with a second, radiopaque material;
processing the precursor stent to remove the plurality of second connectors without adversely affecting the bands and the plurality of first connectors.

14. The method of claim 13, wherein the step of functionally grading the first material and the second, radiopaque material for the at least one of the portion of at least one of the plurality of bands or the at least one of the plurality of first connectors comprises gradually transitioning from the first material to a larger percentage of the second, radiopaque material than the first material as layers of the at least one of the portion of at least one of the plurality of bands or the at least one of the plurality of first connectors are added and then gradually transitioning back from a larger percentage of the second, radiopaque material than the first material to the first material as layers are added, such as to minimize the formation of second phase intermetallic compounds in the at least one of the portion of at least one of the plurality of bands and the at least one of the plurality of first connectors.

15. The method of claim 13, wherein the at least one of the portion of at least one of the plurality of bands or at least one of the plurality of first connectors comprises at least one of a strut of the at least one of the plurality of bands.

16. The method of claim 13, wherein the at least one of the portion of at least one of the plurality of bands or at least one of the plurality of first connectors comprises at least one of the plurality of first connectors.

17. A precursor stent comprising:
a plurality of bands made of a first material disposed adjacent to each other; and a plurality of first connectors connecting each band to an adjacent band and a plurality of second connectors connecting each band to an adjacent band, wherein the plurality of first connectors are configured to remain and the plurality of second connectors are made by functionally grading the first material with a second material to create embrittlement such that the second plurality of connectors are configured to be removed.

18. The precursor stent of claim 17, wherein the second material is a radiopaque material.

19. The precursor stent of claim 17, wherein the plurality of second connectors include abrupt transitions between the first material and the second material to impart embrittlement at junctions of each of the second plurality of connectors and a corresponding band of the plurality of bands.

20. The precursor stent of claim 17, wherein the plurality of second connectors include detrimental second phase intermetallic compounds to impart embrittlement in the second plurality of connectors.

21. A medical device comprising:
    a plurality of bands made of a first material disposed adjacent to each other; and
    at least one connector connecting each band to an adjacent band, wherein the at least one connector is made by functionally grading the first material with a second, radiopaque material.

22. The medical device of claim 21, wherein second phase intermetallic compounds are minimized in the at least one connector.

23. The medical device of claim 21, wherein the medical device is a stent.

24. A medical device comprising:
    a plurality of bands made of a first material disposed adjacent to each other; and
    at least one connector connecting each band to an adjacent band,
    wherein at least a portion of at least one of the bands is made by functionally grading the first material with a second, radiopaque material.

25. The medical device of claim 24, wherein the medical device is a stent.

26. The medical device of claim 25, wherein the plurality of bands includes struts and crowns, with adjacent struts coupled to each other by a corresponding crown, wherein the at least one portion of the at least one band is a strut of the at least one band.

27. The medical device of claim 26, wherein second phase intermetallic compounds are minimized in the strut.

* * * * *